United States Patent [19]

Spector

[11] Patent Number: 4,549,250
[45] Date of Patent: Oct. 22, 1985

[54] NIGHT LIGHT ASSEMBLY

[76] Inventor: Donald Spector, 380 Mountain Rd., Union City, N.J. 07087

[21] Appl. No.: 666,386

[22] Filed: Oct. 30, 1984

[51] Int. Cl.$^4$ ............................................. F21V 33/00
[52] U.S. Cl. ...................... 362/96; 362/101; 362/226; 362/294; 362/311; 362/318; 362/806
[58] Field of Search .............. 362/101, 226, 806, 218, 362/294, 300, 301, 307, 311, 96, 318

[56] References Cited

U.S. PATENT DOCUMENTS

| | | | |
|---|---|---|---|
| 3,248,530 | 4/1966 | Titmas | 362/101 |
| 3,443,083 | 5/1969 | Curran | 362/101 |
| 3,531,635 | 9/1970 | Hancock | 362/101 |
| 3,780,260 | 12/1973 | Elsner | 362/101 |
| 4,070,777 | 1/1978 | LoGiudice | 362/101 |
| 4,072,855 | 2/1978 | Marchese | 362/101 |
| 4,163,998 | 8/1979 | Anderson et al. | 362/252 |
| 4,493,011 | 1/1985 | Spector | 362/101 |

FOREIGN PATENT DOCUMENTS 0815014  3/1981  U.S.S.R. .............................. 362/101

Primary Examiner—Stephen J. Lechert, Jr.
Assistant Examiner—Howard J. Locker
Attorney, Agent, or Firm—Michael Ebert

[57] ABSTRACT

A night light assembly which plugs directly into an electrical wall outlet to provide low level illumination while at the same time generating an aromatic vapor whose odor is thematically related to a replaceable picture slide incorporated in the assembly and illuminated thereby. The assembly includes a shell supported by a plug projecting from its rear and insertable into the wall outlet. Housed in the shell is a low-wattage bulb, the shell being covered by a removable frame within which is nested the picture slide to be illuminated. Coated on the rear face of the slide is a translucent layer having a volatile aromatic liquid dispersed therein. The shell is vented, and as the air in the shell is heated and expanded by heat arising from the bulb, a convection current is produced which passes across the slide layer to volatilize the liquid, thereby creating an aromatic vapor which is discharged through the vent into the atmosphere.

9 Claims, 8 Drawing Figures

NIGHT LIGHT ASSEMBLY

BACKGROUND OF INVENTION

1. Field of Invention

This invention relates generally to night lights to provide low-level illumination in a room or passageway, and more particularly to a night light assembly which incorporates a replaceable picture slide that is illuminated by a low-wattage bulb, the rear face of the slide having a translucent layer thereon containing an aromatic liquid which is volatilized by heat arising from the bulb to exude an aroma that is thematically related to the picture.

2. State of the Art

A bedroom which is excessively bright or which has a disagreeable odor is not conducive to sleep. Hence in considering the sleeping conditions of a room, one must not only seek to minimize noise and other disturbances, but one must also arrange for the proper degree of lighting and take steps to ensure a pleasing atmosphere.

A totally dark room is not the ideal environment for sleeping, for it may be psychologically depressing to the occupant. Moreover, should the sleeper awaken and then move about the dark room, he may collide with furniture and other articles therein. Where the sleeping room is a child's nursery, a minimum degree of light is desirable. Young children are often fearful of complete darkness; and should a parent wish to check on the sleeping child without turning on the room light, a low-level night light which is already "on" is useful for this purpose.

The prevailing atmosphere of a room is a more subtle factor in regard to sleep. However well cleaned a room, if it has carpeting, draperies or other fabrics, these tend to retain odors such as stale tobacco smoke. Hence it is often the practice to make use in bedrooms or nurseries of commercially available air fresheners.

The conventional night light consists of an electrical socket which is integrated with a plug to be inserted into an electrical wall outlet, a low-wattage bulb being held in the socket which also supports a small shade. A night light of this type which provides low-level illumination, is purely utilitarian in function and appearance, and it makes no useful or decorative contribution to the room apart from low-level illumination.

The use of light bulbs to illuminate a picture slide is commonplace, for all commercial slide projectors include a light bulb to supply the required light. And the use of light bulbs as heat sources to volatilize an aromatic liquid held in a pan or impregnating a porous pad is also well known, as evidenced by the patents to Eisner U.S. Pat. No. 2,374,371; Gudeman, U.S. Pat. No. 1,403,648, and Schlesinger, U.S. Pat. No. 2,435,757.

But it has not heretofore been known to combine a low-level night light with a picture slide to provide illumination in a decorative form and an aroma generator to render the atmosphere of the room being illuminated more pleasing.

SUMMARY OF INVENTION

In view of the foregoing, the main object of this invention is to provide a night light assembly which plugs directly into an electrical wall outlet to produce low level illumination while at the same time generating an aromatic vapor whose odor is thematically related to a picture slide incorporated in the assembly and illuminated thereby.

More particularly, an object of this invention is to provide an assembly of the above type in which the picture slide is readily replaceable when its fragrance source is exhausted or when one wishes to change the picture presentations and its thematically-related odor.

Also an object of this invention is to provide an assembly of the above type which is of simple design and which may be manufactured and sold at relatively low cost.

Briefly stated, these objects are attained in a night light assembly which plugs directly into an electrical wall outlet to provide low level illumination while at the same time generating an aromatic vapor whose odor is thematically related to a replaceable picture slide incorporated in the assembly and illuminated thereby.

The assembly includes a shell supported by a plug projecting from its rear and insertable into the wall outlet. Housed in the shell is a low-wattage bulb, the shell being covered by a removable frame within which is nested the picture slide to be illuminated. Coated on the rear face of the slide is a translucent layer having a volatile aromatic liquid dispersed therein. The shell is vented, and as the air in the shell is heated and expanded by heat arising from the bulb, a convection current is produced which passes across the slide layer to volatilize the liquid, thereby sealing an aromatic vapor which is discharged through the vent into the atmosphere.

OUTLINE OF THE DRAWINGS

For a better understanding of the invention as well as other objects and further features thereof, reference is made to the following detailed description to be read in conjunction with the accompanying drawings, wherein.

Figure 4:
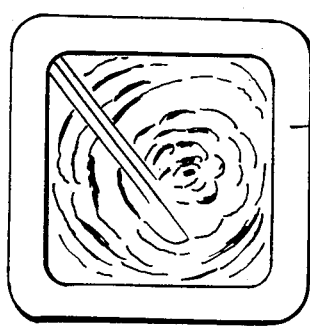
Figure 5:
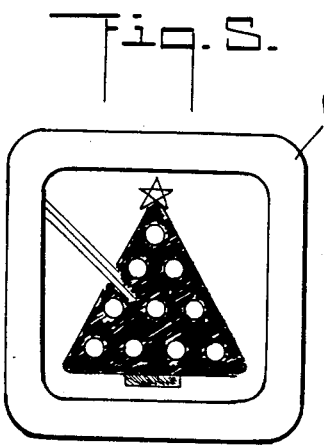
Figure 6:
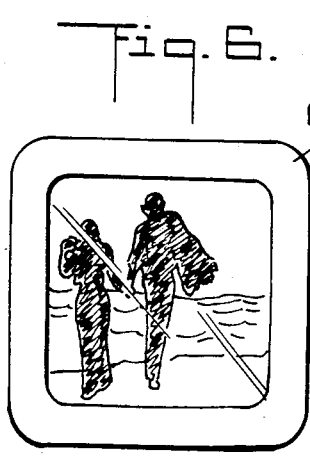

FIG. 4 separately shows a slide having a rose theme;

FIG. 5 separately shows a slide having a Christmas theme;

FIG. 6 shows a slide having a fruit theme; .

Figure 7:
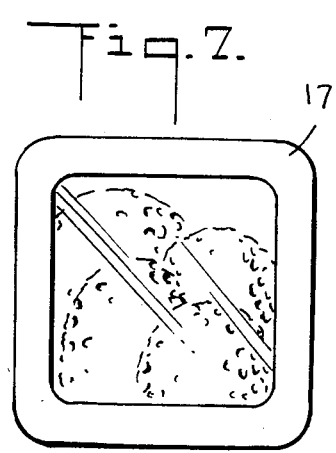

FIG. 7 shows a slide having a sea breeze theme; and

FIG. 8 schematically illustrates the essential elements of the assembly and their functions.

DESCRIPTION OF THE INVENTION

Figure 1:
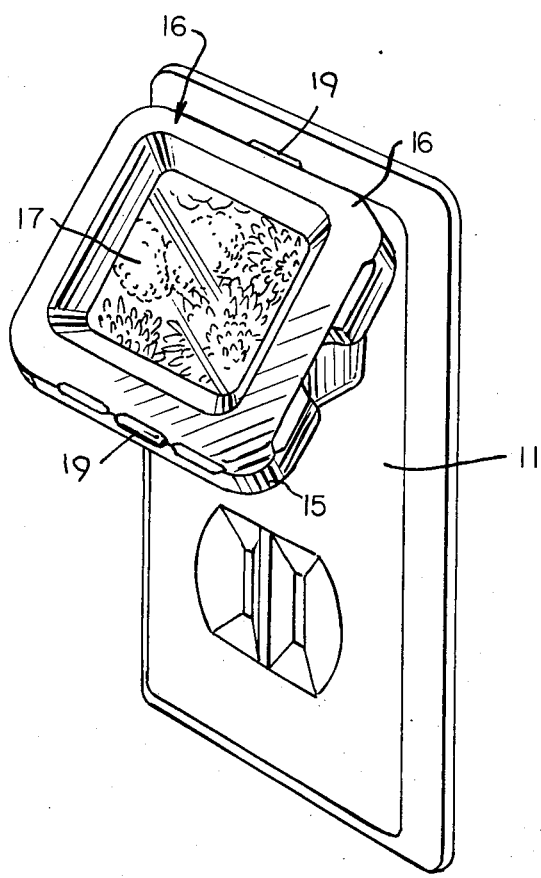
FIG. 1 is a perspective view of a night light assembly in accordance with the invention, the assembly being plugged into an electrical wall outlet.

Referring now to FIG. 1, there is illustrated a night light assembly in accordance with the invention, generally designated by numeral 10. The assembly is plugged into one socket of a standard double socket electrical power outlet 11 located on the baseboard in a bedroom, a nursery or any other room or passageway in which the use of a night light is needed to provide low-level illumination for reasons of safety or for any other purpose.

Figure 3:
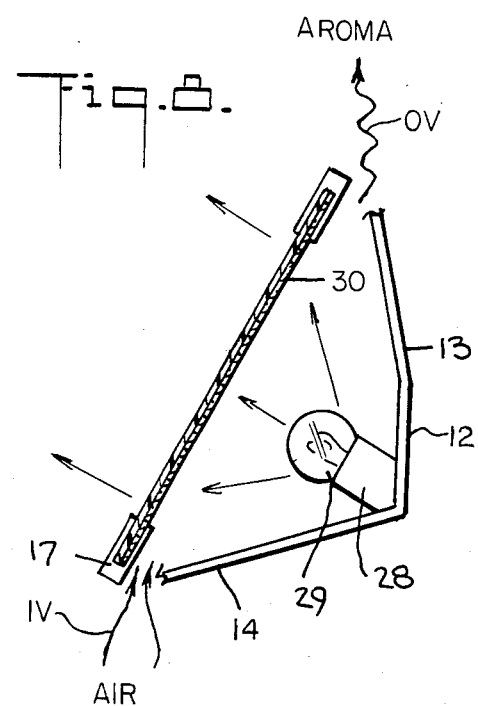
FIG. 3 is a section taken through the assembly.
Figure 2:
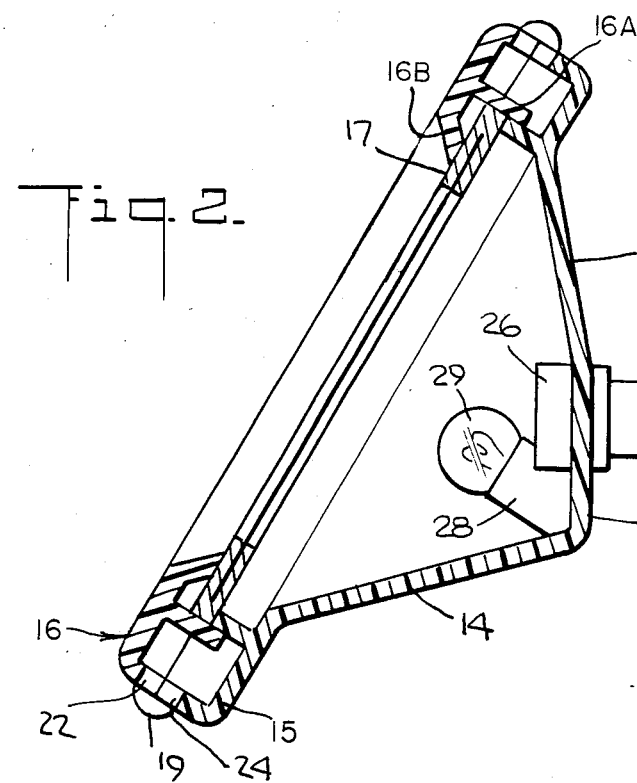
FIG. 2 is an exploded view of the assembly.
Figure 3:
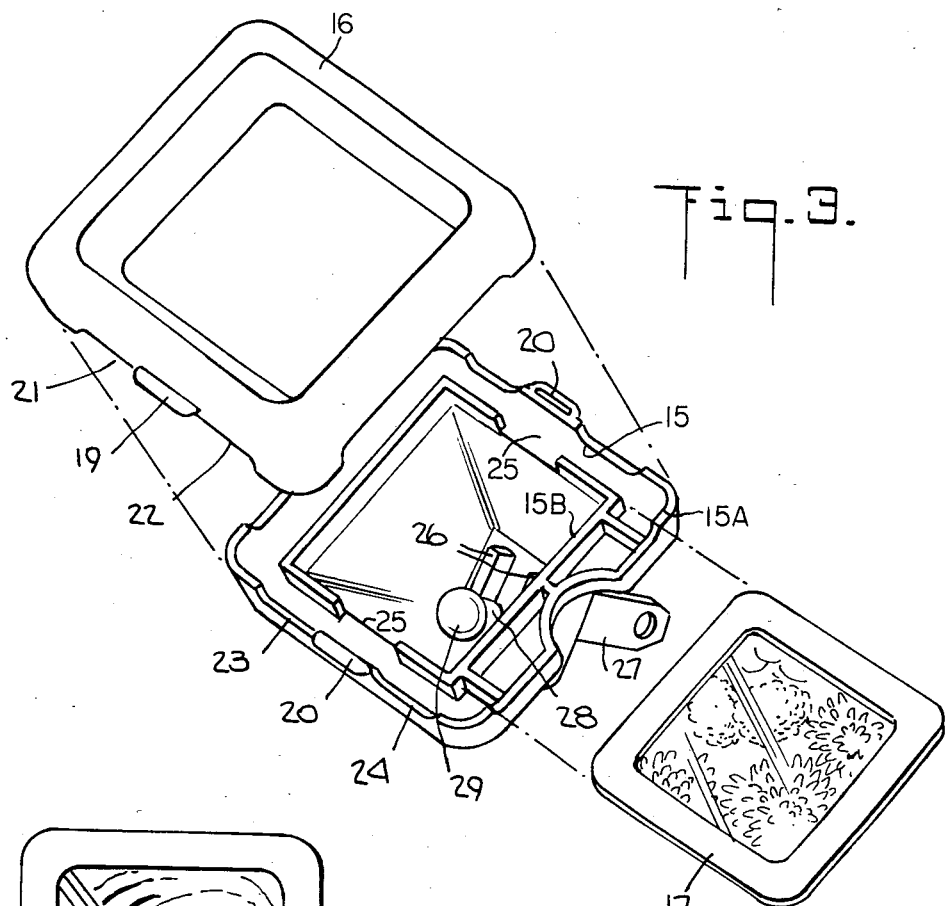

As shown in FIGS. 2 and 3, the assembly includes a shell molded of PVC or other synthetic plastic material such as polyethylene or polycarbonate which is electrically insulating and has good structural properties. The shell includes a rear wall 12, an almost vertical upper wall 13, and a sloped lower wall 14. The rim of the shell is in the form of a square flange 15 having a channel formation defined by an outer ridge 15A and an inner ridge 15B.

The shell is covered by a square frame 16 which is adapted to snap onto flange 15. Frame 16 has a transparent picture slide 17 nested therein within a square inner bank 16A, the frame including a curved-in outer bank 16B which acts as a stop for the slide. Frame 16, which may be molded of the same plastic material as the shell, is provided at its upper and lower sides with flexible center tabs 19 adapted to snap on to complementary upper and lower latching elements 20 formed on the outer ridge of shell flange 15.

Notches 21 and 22 on either side of the upper and lower tabs 19 cooperate with corresponding notches 23 and 24 on either side of latching element 20 to define inlet and outlet vents to permit the flow of air through the shell as indicated by arrows IV and OV. The inner shell ridge 15B is provided with upper and lower center notches 25 to permit air flow through the shell across the rear surface of the slide which covers the shell.

Mounted on rear wall 12 of the shell are a pair of connectors 26 from whose flat prongs 27 project rearwardly to form the plug of the assembly. This serves to support the assembly when the prongs are inserted into the corresponding openings in the wall power outlet 11.

Mounted within the shell on rear wall 12 is a socket 28 having a low-wattage bulb 29 screwed therein. The shell configuration is such that when the assembly is plugged into a vertically-positioned power outlet, frame 16 and slide 17 held thereon are tilted upwardly so that if the outlet is disposed on a baseboard, the slide may be viewed by looking down toward the baseboard. Alternatively, the plug may be connected to the shell by means of a swivel, making it possible to tilt the shell in any direction.

The shell is formed of white plastic or the inner surface thereof is coated with a white or other light reflecting layer. Thus, light emitted from the bulb is reflected by the inner surface of the shell to more or less uniformly irradiate the rear face of slide 17 to provide an illuminated picture which, in addition to being decorative, affords low level illumination in the room.

The rear face of the slide has a thin translucent layer 30 thereon, as shown in FIG. 8, which contains a volatile fragrance that is volatilized by heat emanating from lamp 29. This layer may be formed by a gel having a volatile aromatic liquid dispersed therein. A gel is a two phase colloidal system consisting of a solid and a liquid, the gel behaving as an elastic solid which retains its shape. Use is made for present purposes of a gel having a low solid content and a volatile liquid which is aromatic.

Alternatively, instead of a gel, one may coat the rear surface of the slide with a thin layer of a translucent soft vinyl plastisol containing a fragrance or other volatile organic substance of the type disclosed in the Paciorek et al. U.S. Pat. No. 3,685,734.

As used herein, the term "aroma" is not limited to pleasant or savory smells, but encompasses scents that function as insecticides, air fresheners, deodorants or any other odor that acts to condition, modify or otherwise charge the atmosphere. The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with alcohol.

In FIG. 1, the slide 17 which is illustrated has a picture of a cluster of flowers, and in this instance, the aromatic liquid dispersed in this layer is thematically related to this picture; that is, it yields the characteristic odor of the flowers shown.

The slide is replaceable; and when one uses a slide as shown in FIG. 4 which pictures a rose, then the aroma generated by the layer is that of roses. If the slide in place has a picture of a Christmas tree, as shown in FIG. 5, then a pine-like aroma will be generated; whereas if the picture is that of strawberries, as in the FIG. 7 slide, then a strawberry odor will be exuded by the assembly. Thus, whatever the theme of the picture, the layer produces a thematically-related odor. The FIG. 6 slide shows a sea scene and the related odor is such as to suggest a sea breeze.

Thus, the pictures in the slides will in all cases be of some object having a characteristic odor, and the layer coated on the rear face of the slide will incorporate an aromatic liquid which when vaporized produces this odor, so that the viewer smells, as it were, what he sees.

Thus, the night light assembly is both decorative and useful, and it affords low-level illumination accompanied by an aroma thematically-related to the illuminated picture.

While there has been shown and described a preferred embodiment of NIGHT LIGHT ASSEMBLY in accordance with the invention, it will be appreciated that many changes and modifications may be made therein without, however, departing from the essential spirit thereof.

I claim:

1. A night light assembly comprising:
   A. a shell supported by an electrical plug projecting from the rear thereof which is insertable in a wall electrical outlet;
   B. a socket housed in said shell to receive a low-wattage bulb which is thereby connected to said plug to produce light, said shell having upper and lower vents to permit the flow of air therethrough; and
   C. a removable frame having a picture slide nested therein covering the shell, the rear face of the slide having a translucent layer thereon in which there is dispersed a volatile aromatic liquid that is embedded in the layer whereby when the slide is illuminated by light from said bulb, heat emanating from the bulb produces a convection current in said shell which passes between said upper and lower vents and flows across the exposed surface of said layer to volatilize the liquid embedded therein and generate an aromatic vapor which is discharged through the upper vent.

2. An assembly as set forth in claim 1, wherein said picture has a given theme, and the layer produces an odor which is thematically related thereto.

3. An assembly as set forth in claim 2, wherein said theme is floral, and said odor is the odor of the flower displayed in said picture.

4. An assembly as set forth in claim 2, wherein said picture is that of a given fruit, and said odor is characteristic thereof.

5. An assembly as set forth in claim 1, wherein said shell is provided with a square flange, and said frame is square and is provided with upper and lower flexible tabs which latch onto complementary latching elements on said flange.

6. An assembly as set forth in claim 5, wherein said frame and flange are provided with upper and lower notches on either side of said tabs to define upper and lower vents.

7. An assembly as set forth in claim 1, wherein said shell is configured to cause the covering frame to tilt upwardly.

8. An assembly as set forth in claim 1, wherein said layer is formed of a gel.

9. An assembly as set forth in claim 1, wherein said layer is formed of a plastisol.

* * * * *